United States Patent [19]

Holtkamp, Sr.

[11] Patent Number: Plant 6,603

[45] Date of Patent: Feb. 14, 1989

[54] AFRICAN VIOLET PLANT NAMED CLAUDIA

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 56,474

[22] Filed: Jun. 1, 1987

[51] Int. Cl.[4] ..... A01H 5/00

[52] U.S. Cl. ..... Plt./69

[58] Field of Search ..... Plt./69

[56] References Cited

U.S. PATENT DOCUMENTS

P.P. 3,148 5/1972 Holtkamp ..... Plt. 69

*Primary Examiner*—James R. Feyrer

*Attorney, Agent, or Firm*—Foley & Lardner, Schwartz, Jeffery, Schwaab, Mack, Blumenthal & Evans

[57] ABSTRACT

An African violet plant named Claudia, characterized by its round, dark pink flowers with frilled edges; upright flower stems, producing a tight bouquet above the foliage; profuse flowering; vigorous growth habit; bright green and shiny leaves; non-dropping flowering habit.

1 Drawing Sheet

The present invention comprises a new and distinct cultivar of African violet plant, botanically known as *Saintpaulia ionantha*, and hereinafter referred to by the cultivar name Claudia.

The new cultivar was referred to during the breeding and selection process by the designation G9/20, and is a product of a planned breeding program. The new cultivar was originated from a cross made by applicant in a controlled breeding program in Haffen, Federal Republic of Germany. The female, or seed parent was a cultivar designated D150/2 red girl. The male, or pollen parent was a cultivar designated D134/11 lilac frilled.

Claudia was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Claudia has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Claudia which in combination distinguish this African violet as a new and distinct cultivar:

1. Round-looking dark pink flowers with frilled edges.
2. Forms a nice bouquet on strong upright flower stems.
3. Each plant has 8–9 stems each of which carries 8 to 10 flowers.
4. Profuse flowering.
5. Seed capsule pushes slightly through.
6. Vigorous grower.
7. Plant saleable 9–10 weeks after potting.

8. Long-lasting, non-dropping flowers.
9. After maturity, the flowers dry off and remain on the peduncle without becoming infected by botrytis.
10. Bright green, serrated leaves.

The accompanying color photographic drawing shows a typical specimen plant of the new cultivar. The colors appearing in the photograph are as true as possible with color illustrations of this type.

In the following description, color references are made to the Royal Horticultural Society Colour Chart (RHS), except where general colors of ordinary significance are referred to. Color values were taken under natural light conditions at approximately 1:00 p.m. in Nashville, Tenn.

Botanical Classification: *Saintpaulia ionantha*, Ramat., cv. Claudia.

Parentage:

*Male parent.*—D134/11 lilac frilled.

*Female parent.*—D150/2 red girl.

Propagation: The new cultivar holds its distinguishing characteristics through successive propagations by leaf cuttings.

Plant: From 11 cm to 13 cm tall when grown in pots, and approximately 25–30 cm in diameter when fully grown. The growth rate is vigorous.

*Leaves.*—Shape: Oval to spear-shaped, with edges slightly serrated. Diameter: 60–65 mm wide and 70–80 mm long. Texture: Slightly velvety and slightly hairy. Ribs and veins: Upperside visible, underside very well pronounced, light green and shiny. Color (upper side): 137A. Color (under side): Between 147C-D. Petioles: Green with purplish touch.

*Flowers.*—Buds: Purple, ball-shaped, hairy, 7–9 mm before opening. Sepals: Five (5) in number, purple-green. Calyx: Funnel-shaped. Peduncle: Strong, upright, purplish brown.

*Individual flowers.*—Size: 40 to 50 mm in diameter. Shape: Round, with wavy, frilled edges. Color (upper side): Between 70A-70B; under cooler conditions and more intensive lighting, the pink color is more intense; the two smaller petals have a purple-red center that radiates out toward the edges. Color (under side): 74C. Borne: Each flower stem carries 9–10 flowers on strong, upright peduncles that are free standing above the leaves. Flowering habit: Flowers 9–10 weeks after potting; flowering very profuse.

*Reproductive organs.*—Stamens: Two (2) in number. Anthers: Two, composed of 4 anther cells, seed capsule pushes slightly through. Filaments: 3–4 mm long, yellowish green, with purple on edge. Pollen Color: Yellow 7A. Styles: 7–8 mm, base of ovary light green. Roots: Establish well, white, turning slightly brownish when older.

Disease resistance: Good.

General Observations: Claudia is a very attractive, vigorous grower with bright, shiny, green leaves that have small serrations. Approximately 9–10 weeks after potting the plant has developed 8–9 strong upright flowerstems which carry 9–10 and more round looking, frilled flowers. The flowers are dark pink, but the 2 smaller petals have a purplish red center that radiates out towards the edges. The flowers are on strong peduncles, which form a compact flower head that is free standing above the leaves. The flowers are long-lasting and non-dropping, and the seed capsule pushes slightly through.

I claim:

1. A new and distinct cultivar of African violet named Claudia, as described and illustrated, and particularly characterized by its round, dark pink flowers with frilled edges; upright flower stems, producing a tight bouquet above the foliage; profuse flowering; vigorous growth habit; bright green and shiny leaves; and long lasting and non-dropping flowering habit.

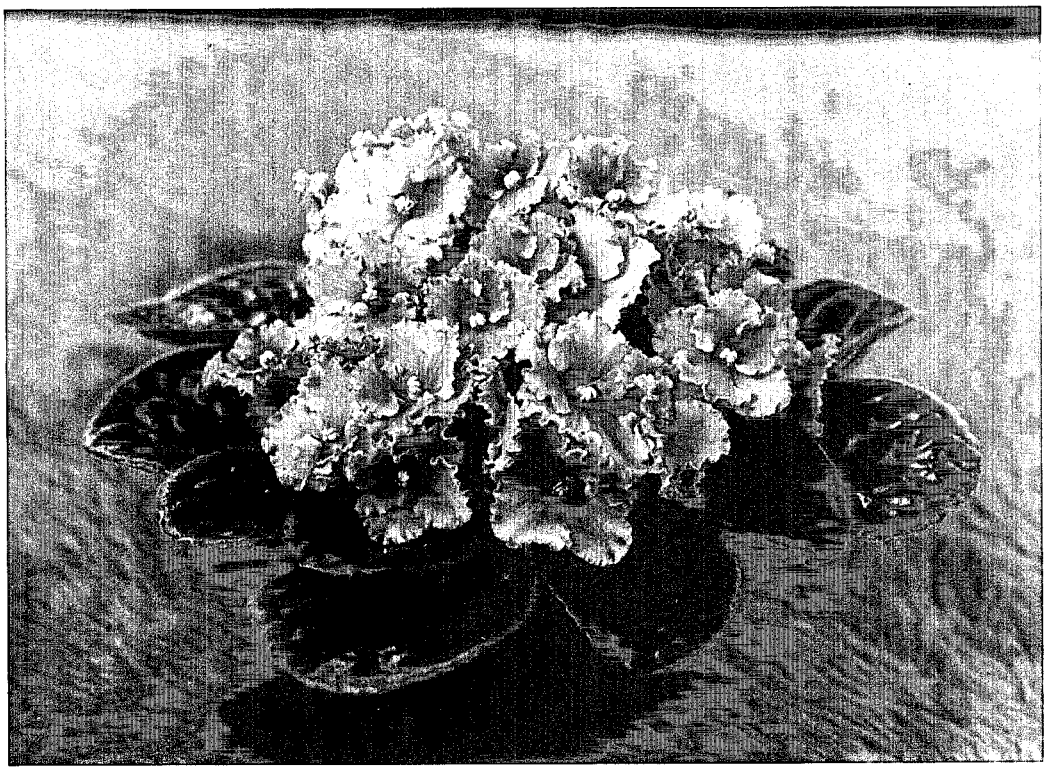

* * * * *